(12) United States Patent
Kusakabe et al.

(10) Patent No.: US 12,357,417 B2
(45) Date of Patent: Jul. 15, 2025

(54) MAGNETIC MARKER SET AND METHOD OF ARRANGING MAGNETIC MARKER

(71) Applicant: MATRIX CELL RESEARCH INSTITUTE INC., Ibaraki (JP)

(72) Inventors: Moriaki Kusakabe, Ibaraki (JP); Naoki Matsumoto, Tochigi (JP); Akio Ota, Tochigi (JP); Masaki Sekino, Tokyo (JP)

(73) Assignee: MATRIX CELL RESEARCH INSTITUTE INC., Ibaraki (JP)

( * ) Notice: Subject to any disclaimer, the term of this patent is extended or adjusted under 35 U.S.C. 154(b) by 0 days.

(21) Appl. No.: 18/285,531

(22) PCT Filed: Jul. 30, 2021

(86) PCT No.: PCT/JP2021/028332
§ 371 (c)(1),
(2) Date: Oct. 4, 2023

(87) PCT Pub. No.: WO2023/007702
PCT Pub. Date: Feb. 2, 2023

(65) Prior Publication Data
US 2024/0180440 A1 Jun. 6, 2024

(51) Int. Cl.
*A61B 90/00* (2016.01)

(52) U.S. Cl.
CPC ...... *A61B 90/39* (2016.02); *A61B 2090/3925* (2016.02); *A61B 2090/3954* (2016.02); *A61B 2090/3987* (2016.02)

(58) Field of Classification Search
CPC ........... A61B 90/39; A61B 2090/3925; A61B 2090/3954; A61B 2090/3987; A61B 5/062
See application file for complete search history.

(56) References Cited

U.S. PATENT DOCUMENTS 11,166,782 B1 * 11/2021 Schermers ............ A61B 90/39
2008/0269601 A1    10/2008 Schwamb
(Continued)

FOREIGN PATENT DOCUMENTS

JP    2008-206578 A    9/2008
JP    2012-531276 A    12/2012
(Continued)

OTHER PUBLICATIONS

International Search Report issued in International Patent Application No. PCT/JP2021/028332, dated Sep. 28, 2021, along with an English translation thereof.

*Primary Examiner* — Sean D Mattson
(74) *Attorney, Agent, or Firm* — Greenblum & Bernstein, P.L.C.

(57) ABSTRACT

A magnetic marker set includes: a magnetic marker including a first rod and a second rod each formed of a stick-shaped ferromagnetic substance, and a stick-shaped third rod; and a needle with a hole in a longitudinal direction thereof. The magnetic marker includes a first connecting portion at which one longitudinal end of the first rod and one longitudinal end of the second rod are rotatably connected, and a second connecting portion at which other longitudinal end of the second rod and one longitudinal end of the third rod are rotatably connected. The magnetic marker is inserted into the hole and has been magnetized such that an orientation of a magnetic field reverses at the first connecting portion. The magnetic marker set includes a draw-in mechanism that brings other longitudinal end of the first rod and other longitudinal end of the third rod into contact with each other.

19 Claims, 11 Drawing Sheets

(56) References Cited

U.S. PATENT DOCUMENTS

| | | | | |
|---|---|---|---|---|
| 2010/0331668 | A1* | 12/2010 | Ranpura | A61B 90/39 |
| | | | | 600/424 |
| 2011/0021888 | A1 | 1/2011 | Sing et al. | |
| 2011/0313288 | A1* | 12/2011 | Chi Sing | A61B 8/0825 |
| | | | | 600/437 |
| 2016/0022266 | A1* | 1/2016 | Lukin | A61B 17/1114 |
| | | | | 606/154 |
| 2016/0354178 | A1* | 12/2016 | Mayes | A61B 5/4312 |
| 2019/0223975 | A1* | 7/2019 | Agostinelli | A61B 90/39 |
| 2021/0153970 | A1* | 5/2021 | Agostinelli | A61B 90/39 |

FOREIGN PATENT DOCUMENTS

| | | |
|---|---|---|
| JP | 2017-521223 A | 8/2017 |
| JP | 2018-526160 A | 9/2018 |
| JP | 2019-146957 A | 9/2019 |

\* cited by examiner

MAGNETIC MARKER SET AND METHOD OF ARRANGING MAGNETIC MARKER

TECHNICAL FIELD

The present invention relates to a magnetic marker set that contains magnetic marker for indicating a target position, and a method of arranging magnetic marker for arranging magnetic marker at a target position.

BACKGROUND ART

Known prior arts of magnetic marker include the technique of Patent Literature 1 and known devices for detecting magnetic marker include the technique of Patent Literature 2.

PRIOR ART LITERATURE

Patent Literature

Patent Literature 1: Japanese Patent Application Laid Open No. 2018-526160
Patent Literature 2: Japanese Patent Application Laid Open No. 2008-206578

SUMMARY OF THE INVENTION

Problems to be Solved by the Invention

Patent Literature 1 makes reference to magnetic markers of various shapes, the material of them, and the like. However, since it does not specify structures suitable for easily detectable magnetic marker or state of magnetization, it is not clear what kind of structure is preferable. An object of the present invention is to provide a magnetic marker that is easily detectable.

Means to Solve the Problems

A magnetic marker set according to the present invention includes: a magnetic marker including a first rod and a second rod each formed of a stick-shaped magnetic substance with residual magnetization characteristics, and a stick-shaped third rod; and a needle with a hole in a longitudinal direction thereof. The magnetic marker further includes a first connecting portion at which one longitudinal end of the first rod and one longitudinal end of the second rod are rotatably connected, and a second connecting portion at which other longitudinal end of the second rod and one longitudinal end of the third rod are rotatably connected. The magnetic marker is inserted into the hole and has been magnetized such that an orientation of a magnetic field reverses at the first connecting portion. The magnetic marker set further includes a draw-in mechanism that brings other longitudinal end of the first rod and other longitudinal end of the third rod close to each other when the magnetic marker is extruded from the hole. A method of arranging magnetic marker using a magnetic marker set according to the present invention executes a needle insertion step and an extrusion step. The needle insertion step inserts the needle with the magnetic marker inserted in the hole such that a tip of the needle lies at a position where the magnetic marker is to be arranged. The extrusion step extrudes the magnetic marker from the hole such that the first connecting portion points toward a device that detects the magnetic marker.

Effects of the Invention

With the magnetic marker set according to the present invention, the magnetic marker is extruded from the needle and the other longitudinal end of the first rod and the other longitudinal end of the third rod come into contact with each other. When the magnetic marker is thus deformed, a triangle is formed by the first rod, the second rod, and the third rod. Since the magnetic marker when inserted in the needle has been magnetized so that the orientation of the magnetic field reverses at the first connecting portion, the orientation of the magnetic field in the first connecting portion becomes substantially the same when the magnetic marker is extruded from the needle and deformed. This strengthens the magnetic field generated by the magnetic marker, thus facilitating its detection.

DETAILED DESCRIPTION OF THE EMBODIMENTS

Figure 1:
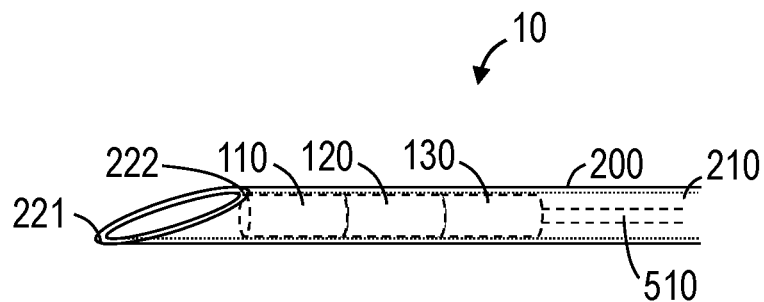
FIG. 1 shows an exemplary configuration of a magnetic marker set.

Embodiments of the present invention are described in detail below. Components with the same function are denoted with the same reference characters and overlapping description is omitted.

Embodiment 1

<Configuration of Magnetic Marker Set>

Figure 2:
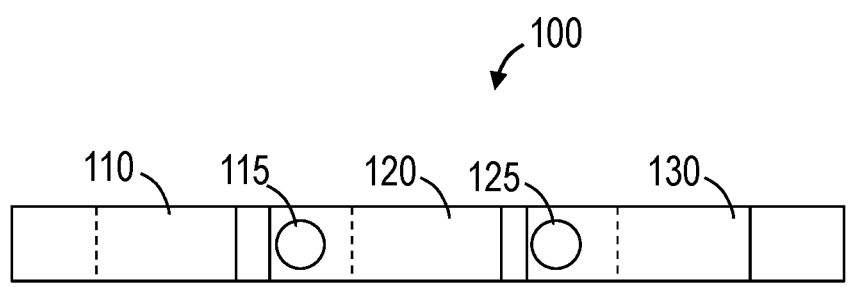
FIG. 2 shows an exemplary configuration of a magnetic marker, illustrating an example where a first rod, a second rod, and a third rod are arranged linearly.
Figure 3:
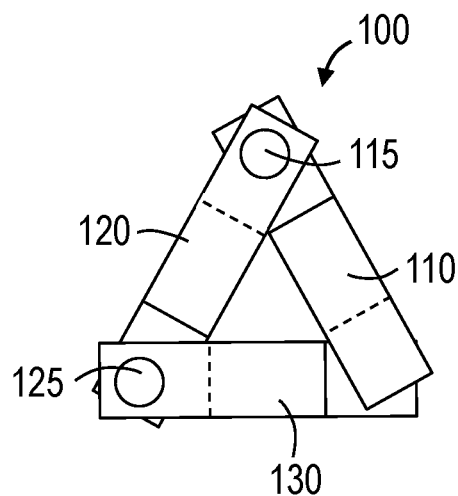
FIG. 3 shows an exemplary configuration of the magnetic marker, illustrating an example where the first rod, the second rod, and the third rod are arranged in a triangle.
Figure 4:
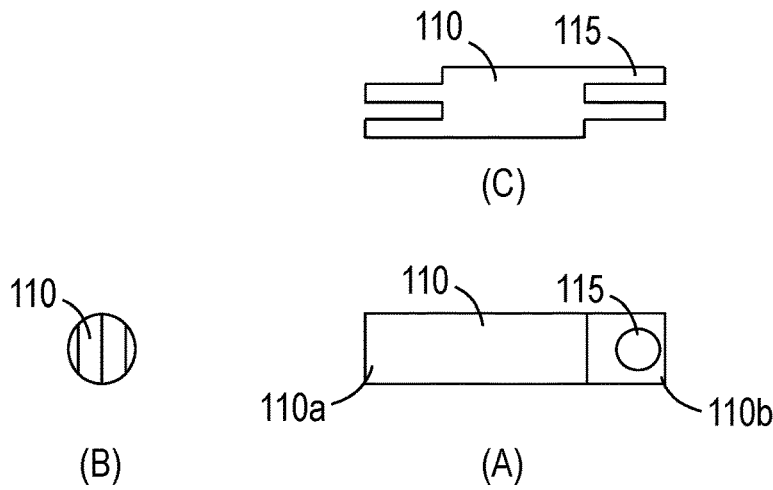
FIG. 4 shows an example of the shape of the first rod.
Figure 5:
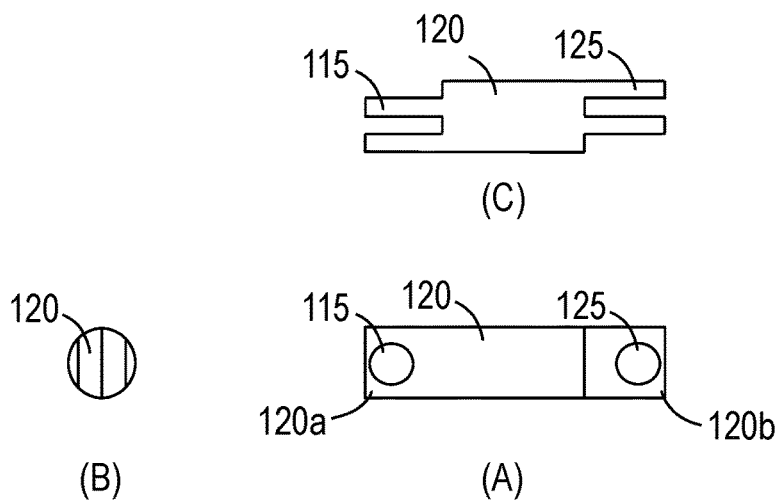
FIG. 5 shows an example of the shape of the second rod.
Figure 6:
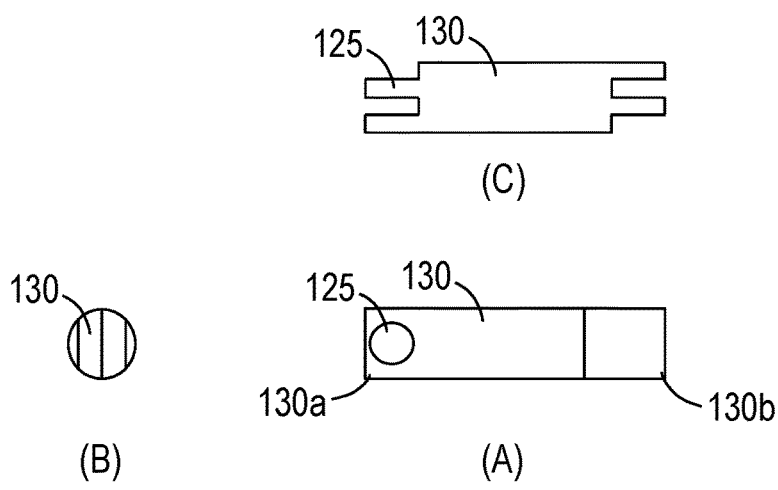
FIG. 6 shows an example of the shape of the third rod.

The inventions described in Patent Literatures 1 and 2 are techniques related to marker for indicating the location of breast cancer and the like. The present invention also includes indicating the location of breast cancer as an object, but it may be used for the purpose of indicating the location of something other. For example, it includes applications intended for animals, rather than human beings. Also, it may be used with some object other than living being. FIG. 1 shows an exemplary configuration of a magnetic marker set. FIG. 2 shows an exemplary configuration of a magnetic marker, illustrating an example where a first rod, a second rod, and a third rod are arranged linearly. FIG. 3 shows an exemplary configuration of the magnetic marker, illustrating an example where the first rod, the second rod, and the third rod are arranged in a triangle. FIG. 4 shows an example of the shape of the first rod, FIG. 5 shows an example of the shape of the second rod, and FIG. 6 shows an example of the shape of the third rod. FIG. 4(A), FIG. 5(A), and FIG. 6(A) are front views. FIG. 4(B), FIG. 5(B), and FIG. 6(B) are left side views. FIG. 4(C), FIG. 5(C), and FIG. 6(C) are plan views.

A magnetic marker set 10 includes: a magnetic marker having a first rod 110 and a second rod 120 each formed of a stick-shaped ferromagnetic substance, and a stick-shaped third rod 130; and a needle 200 with a hole 210 in a longitudinal direction thereof. The third rod 130 may also be ferromagnetic substance or the third rod 130 may be made of non-magnetized material. A magnetic marker 100 further includes a first connecting portion 115 at which a longitudinal end 110b of the first rod 110 and a longitudinal end 120a of the second rod 120 are rotatably connected, and a second connecting portion 125 at which a longitudinal end 120b of the second rod and a longitudinal end 130a of the third rod are rotatably connected. If any member other than the first rod 110 and the second rod 120 is included in the first connecting portion 115, the member may be ferromagnetic substance as well. For example, if a separate shaft is used for rotatably connecting the first rod 110 and the second rod 120, the shaft could be ferromagnetic substance as well. However, if the shaft is small, it does not have to be ferromagnetic substance.

The magnetic marker 100 is inserted into the hole 210 and has been magnetized such that an orientation of a magnetic field reverses at the first connecting portion 115. Since in FIG. 1 the magnetic marker 100 has been inserted into the hole 210, it is linear as shown in FIG. 2. FIG. 1 also shows an extrusion means 510 for extruding the magnetic marker 100 from the hole 210. The extrusion means 510 may be included in the magnetic marker set 10 or may be configured not to be included in the magnetic marker set 10. For example, the extrusion means 510 may be an independent tool which is utilized when the magnetic marker set 10 is used. When used as marker for breast cancer, for example, the first rod 110, the second rod 120, and the third rod 130 each may be about 3 mm in length and about 1 mm in diameter. The dimensions of the magnetic marker 100 may be determined in consideration of ease of arrangement and ease of detection depending on its intended use.

Figure 7:
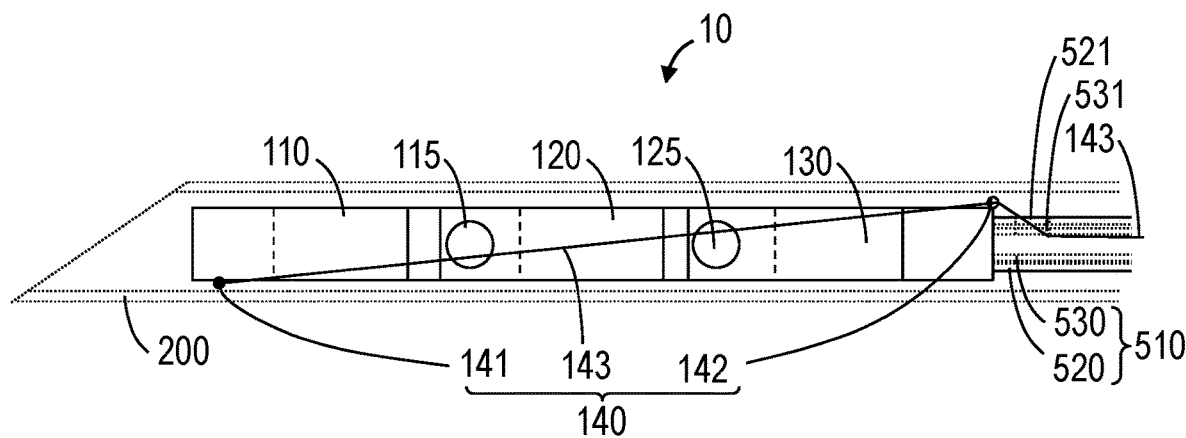
FIG. 7 shows a magnetic marker 100 as inserted in a hole 210.

FIG. 7 shows the magnetic marker 100 as inserted in the hole 210. The magnetic marker set 10 also includes a draw-in mechanism 140, which brings a longitudinal end 110a of the first rod 110 and a longitudinal end 130b of the third rod 130 close to each other when the magnetic marker 100 is extruded from the hole 210. FIG. 7 also shows the draw-in mechanism 140 using a thread 143 and the extrusion means 510 having a cutting means 550 for cutting the thread. However, the present invention is not limited to the draw-in mechanism 140 using the thread 143 shown in FIG. 7; elastic body, shape-memory alloy, and the like may be used to bring the longitudinal end 110a of the first rod 110 and the longitudinal end 130b of the third rod 130 close to each other. "Bringing them close to each other" means not only bringing the longitudinal end 110a of the first rod 110 and the longitudinal end 130b of the third rod 130 into contact with each other but also includes bringing them into the vicinity of each other. They are brought close to each other so that the first rod, the second rod, and the third rod are arranged substantially in a triangle.

The draw-in mechanism 140 may be included in the magnetic marker set 10 as a separate component from the magnetic marker 100 or the magnetic marker 100 itself may include the draw-in mechanism 140. In other words, if the magnetic marker 100 itself has no feature to deform into a triangle, the draw-in mechanism 140 may be included in the magnetic marker set 10 as a separate component from the magnetic marker 100. Alternatively, the magnetic marker 100 itself may be provided with a feature to deform into a triangle (the draw-in mechanism 140). Further, there may be a structure for maintaining the state of the longitudinal end 110a of the first rod 110 and the longitudinal end 130b of the third rod 130 being in contact with each other (the state of the first rod 110, the second rod 120, and the third rod 130 being arranged in a triangle). For example, the longitudinal end 110a of the first rod 110 may be formed like a ball, which may be fitted into a slit formed in the longitudinal end 130b of the third rod 130. Alternatively, a hook may be provided at the longitudinal end 110a of the first rod 110, such that the hook is fitted into a hole formed in the longitudinal end 130b of the third rod 130.

Figure 8:
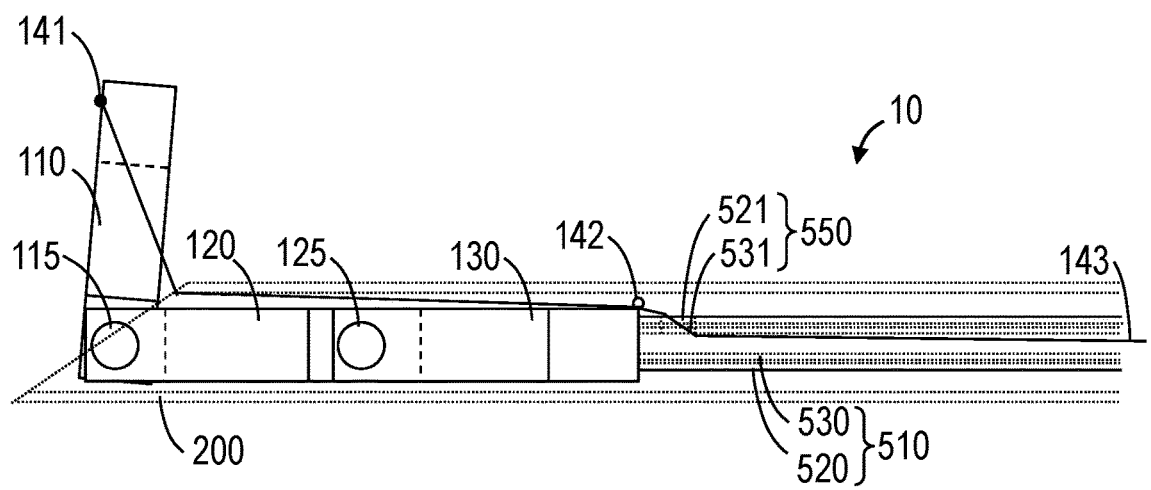
FIG. 8 shows a state where a first rod 110 has been extruded using an extrusion means 510 with tension applied to a thread 143.
Figure 9:
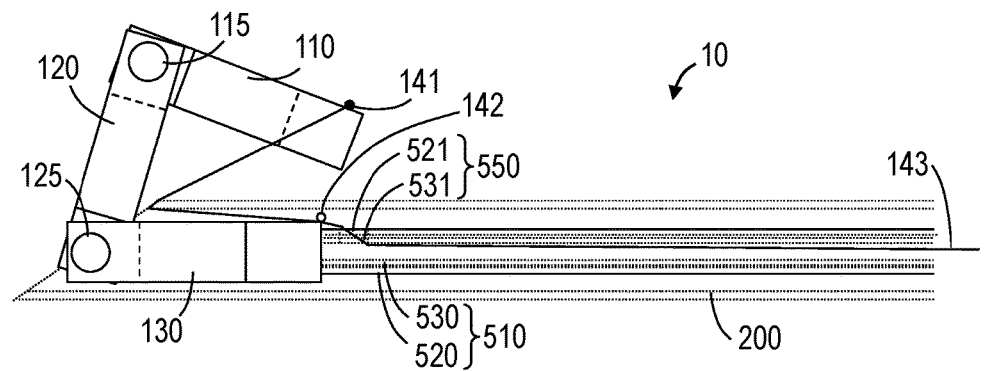
FIG. 9 shows a state where the first rod 110 and a second rod 120 have been extruded using the extrusion means 510 with tension applied to the thread 143.
Figure 10:
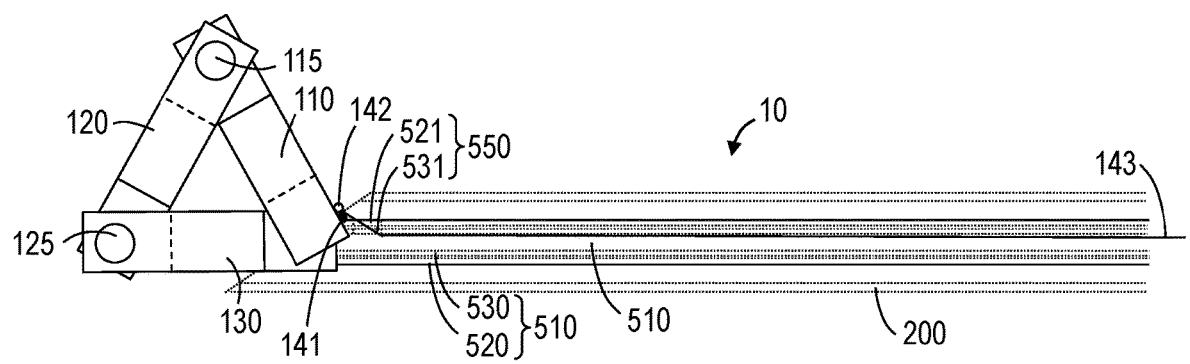
FIG. 10 shows a state where the magnetic marker 100 has been entirely extruded using the extrusion means 510 with tension applied to the thread 143.

FIG. 8 shows a state where the first rod 110 has been extruded using the extrusion means 510 with tension applied to the thread 143. FIG. 9 shows a state where the first rod 110 and the second rod 120 have been extruded using the extrusion means 510 with tension applied to the thread 143. FIG. 10 shows a state where the magnetic marker 100 has been entirely extruded using the extrusion means 510 with tension applied to the thread 143. In FIGS. 7 to 10, the draw-in mechanism 140 has the thread 20) 143 arranged in the hole 210. The magnetic marker 100 is positioned so as to be extruded from the hole 210 in the order of the first rod 110, the second rod 120, and the third rod 130. One end of the thread 143 is fixed to a fixing portion 141 at the longitudinal end 110a of the first rod 110, and the thread 143 is movably held in a holding portion 142 at the longitudinal end 130b of the third rod 130. "Being movably held" means that the thread is free to move in the longitudinal direction like a thread passed through a hole, but is held at the position of the hole (is held at a particular position while being movable in the longitudinal direction). In this example, the draw-in mechanism 140 consists of the thread 143, the fixing portion 141, and the holding portion 142. The draw-in mechanism 140 may also have a mechanism to apply tension to the thread 143. The magnetic marker 100 may also be positioned so as to be extruded from the hole 210 in the order of the third rod 130, the second rod 120, and the first rod 110. In this case, one end of the thread 143 may be fixed to the fixing portion 141 at the longitudinal end 130b of the third rod 130, and the thread 143 may be movably held in the holding portion 142 at the longitudinal end 110a of the first rod 110.

Figure 11:
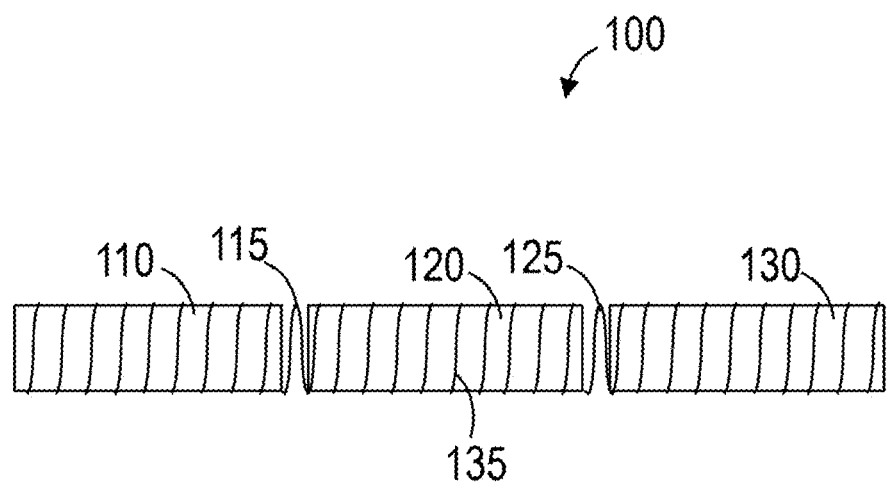
FIG. 11 shows a state where a first connecting portion and a second connecting portion are formed of coil-shaped elastic body and the first rod, the second rod, and the third rod are arranged linearly.
Figure 12:
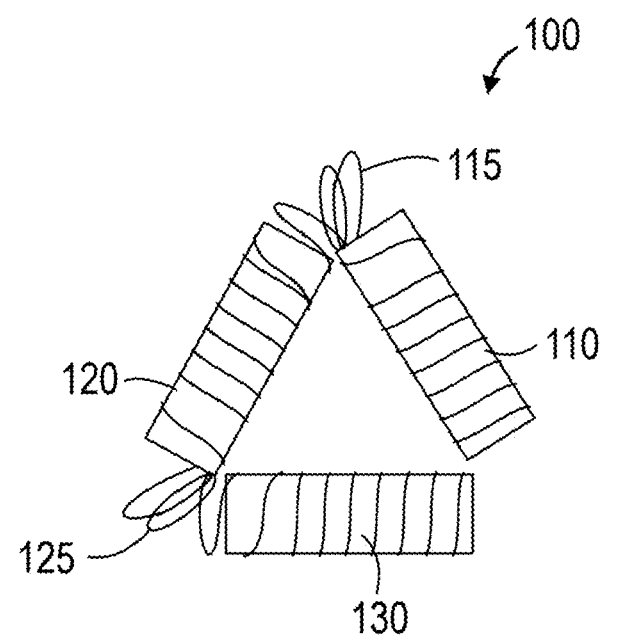
FIG. 12 shows a state where the first connecting portion and the second connecting portion are formed of coil-shaped elastic body and the first rod, the second rod, and the third rod are arranged in a triangle.

FIG. 11 shows a state where a first connecting portion and a second connecting portion are formed of coil-shaped elastic body and the first rod, the second rod, and the third rod are arranged linearly. FIG. 12 shows a state where the first connecting portion and the second connecting portion are formed of coil-shaped elastic body and the first rod, the second rod, and the third rod are arranged in a triangle. In the example of FIGS. 11 and 12, a coil-shaped elastic body 135 is wound around the first rod, the second rod, and the third rod. A portion of the elastic body 135 that connects the first rod and the second rod is the first connecting portion 115 and a portion of the elastic body 135 that connects the second rod and the third rod is the second connecting portion 125. Such structures can also constitute the first connecting portion 115 and the second connecting portion 125. In the case of this configuration, the fixing portion 141 and the holding portion 142 may be formed on the elastic body 135.

Figure 13:
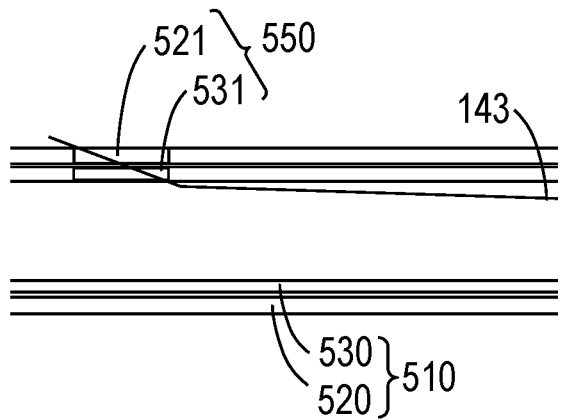
FIG. 13 is a front view showing a state where an inner tube side hole 521 and an inner-inner tube side hole 531 are placed at a position in which they face each other.
Figure 14:
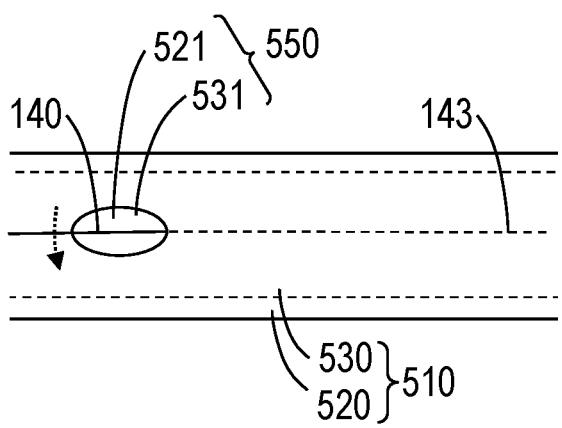
FIG. 14 is a plan view showing a state where the inner tube side hole 521 and the inner-inner tube side hole 531 are placed at the position in which they face each other.
Figure 15:
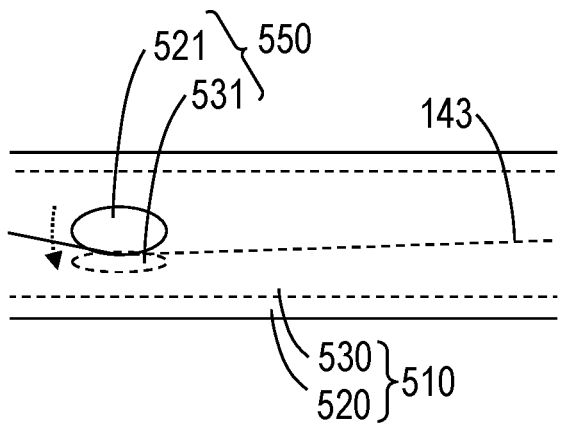
FIG. 15 is a plan view showing a state where the inner tube side hole 521 and the inner-inner tube side hole 531 are placed at a position in which they do not face each other.

The extrusion means 510 shown in FIGS. 7 to 10 is constituted by an inner tube 520 and an inner-inner tube 530. The inner tube 520 has an inner tube side hole 521 and the inner-inner tube 530 has an inner-inner tube side hole 531. The inner tube side hole 521 and the inner-inner tube side hole 531 form the cutting means 550. The inner tube side hole 521 and the inner-inner tube side hole 531 can be placed at a position in which they face each other and a position at which they do not face each other by rotating the inner-inner tube 530. FIG. 13 is a front view showing a state where the inner tube side hole 521 and the inner-inner tube side hole 531 are placed at a position in which they face each other. FIG. 14 is a plan view showing a state where the inner tube side hole 521 and the inner-inner tube side hole 531 are placed at the position in which they face each other. The thread 143 passes through the inner tube side hole 521 and the inner-inner tube side hole 531. FIG. 15 is a plan view showing a state where the inner tube side hole 521 and the inner-inner tube side hole 531 are placed at a position in which they do not face each other. By rotating the inner-inner tube 530, the state of FIG. 14 can be switched to the state of FIG. 15. The thread 143 can be cut by placing the inner tube side hole 521 and the 20) inner-inner tube side hole 531 at the position in which they do not face each other, as in FIG. 15. However, the cutting means for cutting the thread 143 is not limited to this configuration. The thread 143 may be cut with a different configuration, such as installing a sharp tool. Any other configuration is possible as long as it can cut the thread 143 after extruding the magnetic marker 100 from the hole 210 and bringing the longitudinal end 110a of the first rod and the longitudinal end 130b of the third rod into contact with each other.

Figure 16:
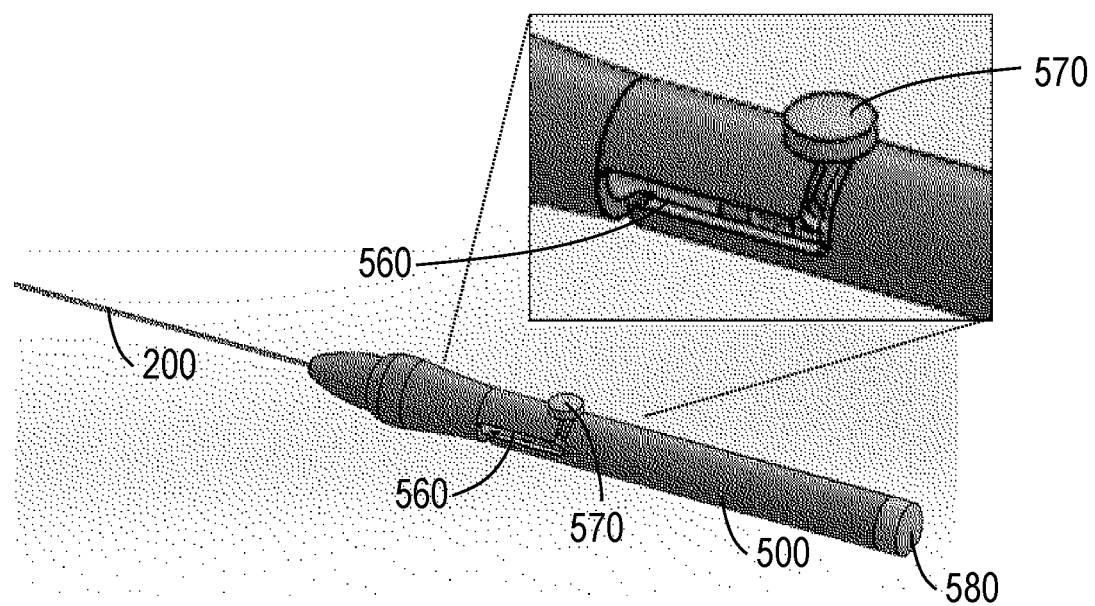
FIG. 16 shows an example of an operational portion of an extrusion means.

FIG. 16 shows an example of an operational portion of an extrusion means. Although a specific internal structure of the extrusion means 510 is not illustrated, it may have an operational portion 500 to be held by a user on the right side in FIGS. 7 to 10. The operational portion 500 has a knob 570. In FIG. 16, an enlarged view of a portion around the knob 570 and a slit 560 is also shown. For example, by rotating the knob 570 by 90 degrees along the slit 560, the user places the magnetic marker 100 into an extrudable state. Then, the user longitudinally moves the knob along the slit 560 to extrude the magnetic marker 100 from the hole 210. Then, by rotating the knob 570 along the slit 560 further 90 degrees, the user rotates the inner-inner tube 530 and cuts the thread 143. For example, if the thread 143 is connected to the interior of an end portion 580 via elastic body, tension can be applied to the thread 143. However, the present invention is not limited to the configuration of FIG. 16. Other configurations are also possible.

<Magnetization of Magnetic Marker>

Figure 17:
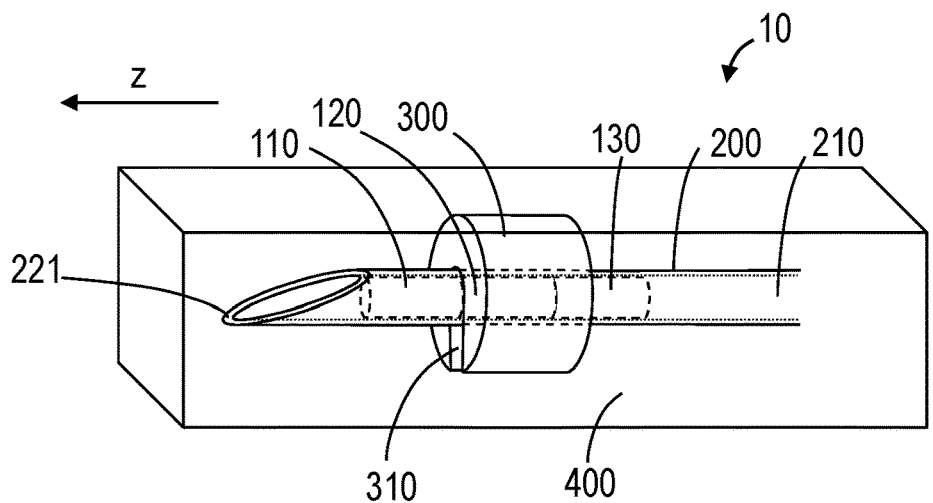
FIG. 17 shows an arrangement for magnetizing magnetic marker.
Figure 18:
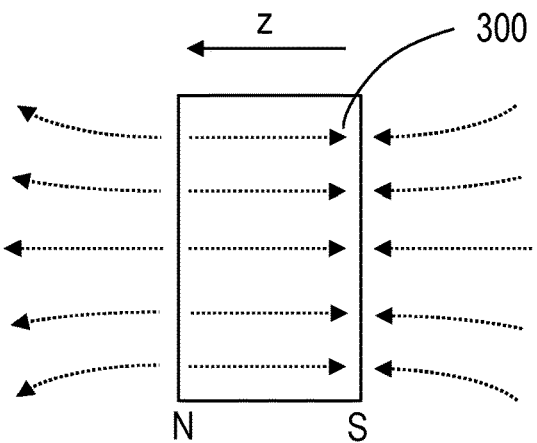
FIG. 18 depicts a magnetic field of a permanent magnet.
Figure 19:
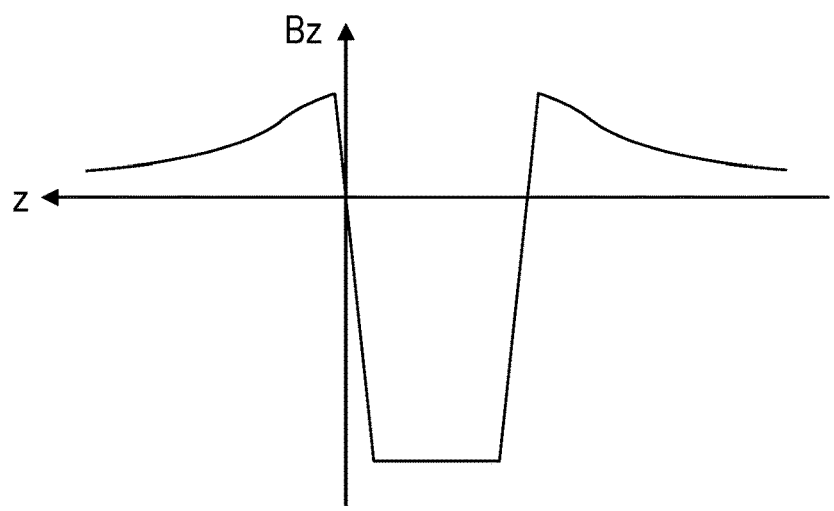
FIG. 19 depicts magnetic flux density around a center line of the permanent magnet.

FIG. 17 shows an arrangement for magnetizing magnetic marker. FIG. 18 depicts a magnetic field of a permanent magnet. FIG. 19 depicts magnetic flux density around a center line of the permanent magnet. The magnetic marker set 10 shown in FIG. 17 also includes a permanent magnet 300 and an accommodation means 400. The permanent magnet 300 is in the shape of a plate with one face being the N pole and the other face being the S pole, and has a slit 310 penetrating from the one face to the other face.

The accommodation means 400 holds the needle 200 having the magnetic marker 100 inserted therein, with the needle 200 inserted in the slit 310 such that either face of the permanent magnet 300 aligns with the position of the first connecting portion 115. By thus positioning the permanent magnet 300, the magnetic marker 100 can be magnetized so that the orientation of the magnetic field reverses at the first connecting portion 115. A thickness of the permanent magnet 300 is preferably substantially the same as the length of the second rod 120, but it can be half the length of the second rod 120 or more. In practice, the thickness of the permanent magnet 300 can be equal to or more than the length of the second rod 120 to equal to or less than the sum of the length of the second rod 120 and half the length of the third rod. The needle 200 should be inserted so that the second rod 120 is located in the slit 310. The first rod 110, the second rod 120, and the first connecting portion 115 are formed of ferromagnetic substance. The material of them preferably has a coercive force of 100 Oe or more. Magnetic substance having strong coercive force and residual magnetization characteristics is desirable because it facilitates maintaining a magnetized magnetic field. Note that the horizontal axis in FIG. 19 indicates position on the Z axis and the vertical axis indicates magnetic flux density. For breast cancer, for example, sufficient magnetization is possible when the maximum value of the magnetic flux density in the positive direction is 80 milliTesla (mT) and the maximum value in the negative direction is −200 milliTesla (mT).

Figure 20:
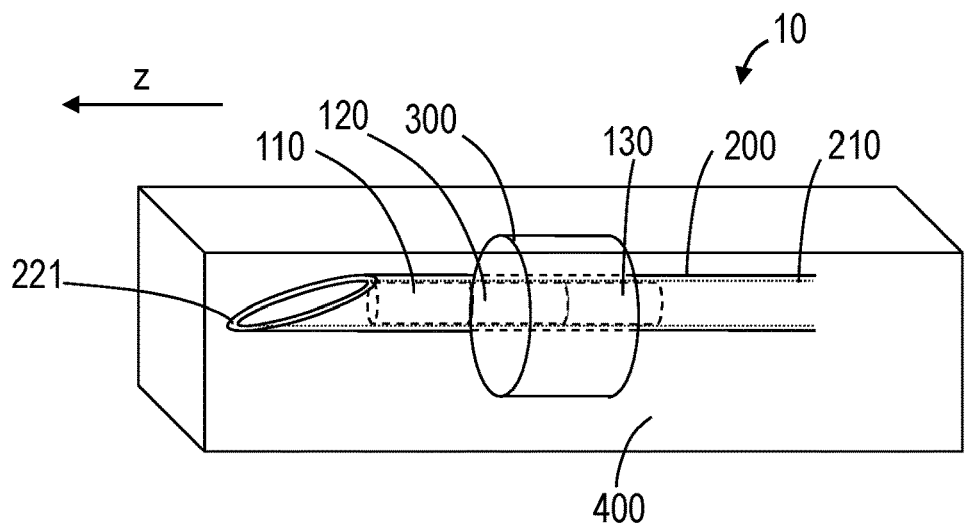
FIG. 20 shows another arrangement for magnetizing magnetic marker.

FIG. 20 shows another arrangement for magnetizing magnetic marker. The permanent magnet 300 shown in the drawing does not have the slit 310. In this drawing, the permanent magnet 300 is in the shape of a plate with one face being the N pole and the other face being the S pole. Then, the accommodation means 400 holds the needle 200 having the magnetic marker 100 inserted therein, with the needle 200 positioned such that the position of the first connecting portion 115 is on the same plane as either face of the permanent magnet 300 and that the normal direction of the plane coincides with the longitudinal direction of the second rod 120. Either in the case of FIG. 17 or FIG. 20, the needle 200 is held so that the second rod 120 is at the position of the permanent magnet 300. Although one permanent magnet 300 is used in FIG. 20, multiple permanent magnets 300 may be arranged around the needle 200. The magnetization method shown in FIG. 17 is considered to be preferable as the way of magnetizing the magnetic marker 100. However, the magnetization method shown in FIG. 20 is also possible as long as it is capable of sufficient magnetization.

Figure 21:
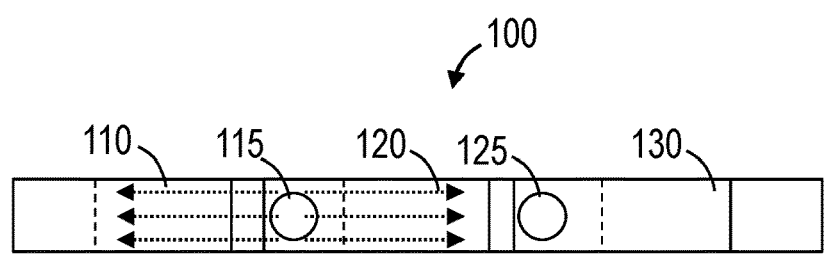
FIG. 21 depicts the magnetic field within magnetic marker in magnetized state.
Figure 22:
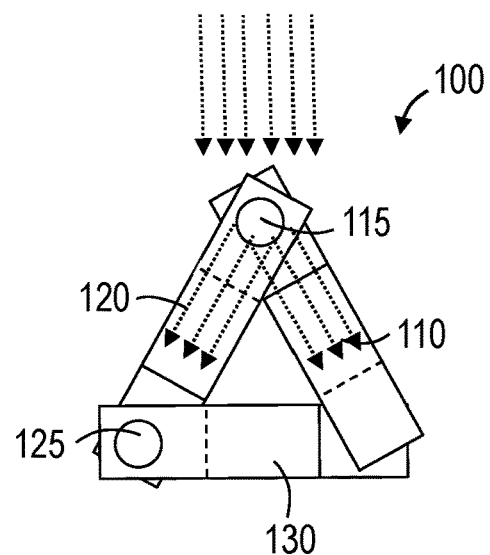
FIG. 22 depicts the magnetic field with the first rod, the second rod, and the third rod arranged in a triangle (with the other longitudinal end of the first rod and the other longitudinal end of the third rod being in contact with each other).
Figure 23:
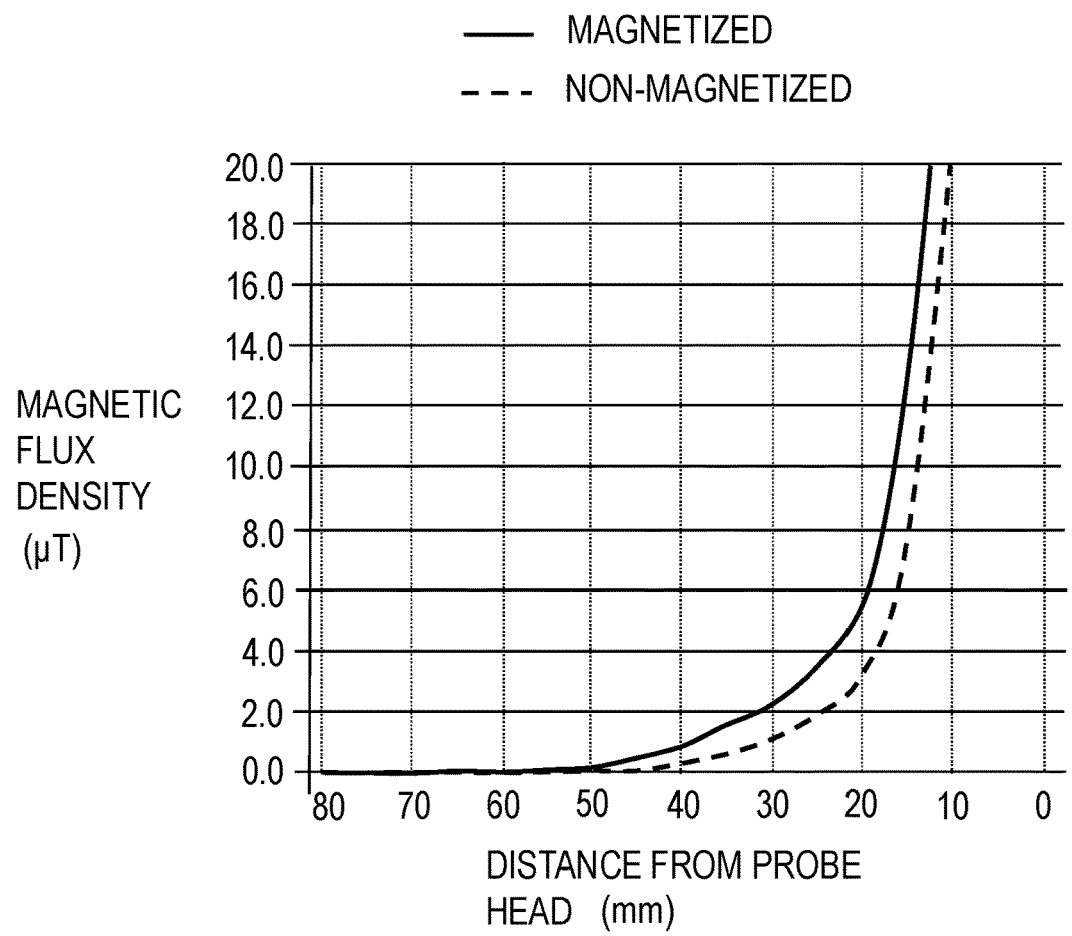
FIG. 23 shows results of observing the magnetic flux density from the upper side of FIG. 22.

FIG. 21 depicts the magnetic field within magnetic marker in magnetized state. FIG. 22 depicts the magnetic field with the first rod, the second rod, and the third rod arranged in a triangle (with the other longitudinal end of the first rod and the other longitudinal end of the third rod being in contact with each other). With the magnetic marker set 10, the magnetic marker 100 is extruded from the needle 200 and the longitudinal end 110a of the first rod 110 and the longitudinal end 130b of the third rod 130 come into contact with each other. When the magnetic marker 100 is thus deformed, a triangle is formed by the first rod 110, the second rod 120, and the third rod 130. Since the magnetic marker 100 when inserted in the needle 200 has been magnetized so that the orientation of the magnetic field reverses at the first connecting portion 115, the orientation of the magnetic field in the first connecting portion 115 becomes substantially the same when the magnetic marker 100 is extruded from the needle 200 and deformed. This strengthens the magnetic field generated by the magnetic marker 100, thus facilitating its detection. FIG. 23 shows the results of observing the magnetic flux density from the upper side of FIG. 22 using the device for detecting magnetic marker shown in Patent Literature 2. The horizontal axis indicates the distance from the probe head of the device for detecting magnetic marker to the magnetic marker, and the vertical axis indicates the magnetic flux density. It can be seen that when the magnetic marker 100 is magnetized in the manner shown in FIG. 22, the magnetic flux is easy to detect even at a greater distance from the probe.

Figure 24:
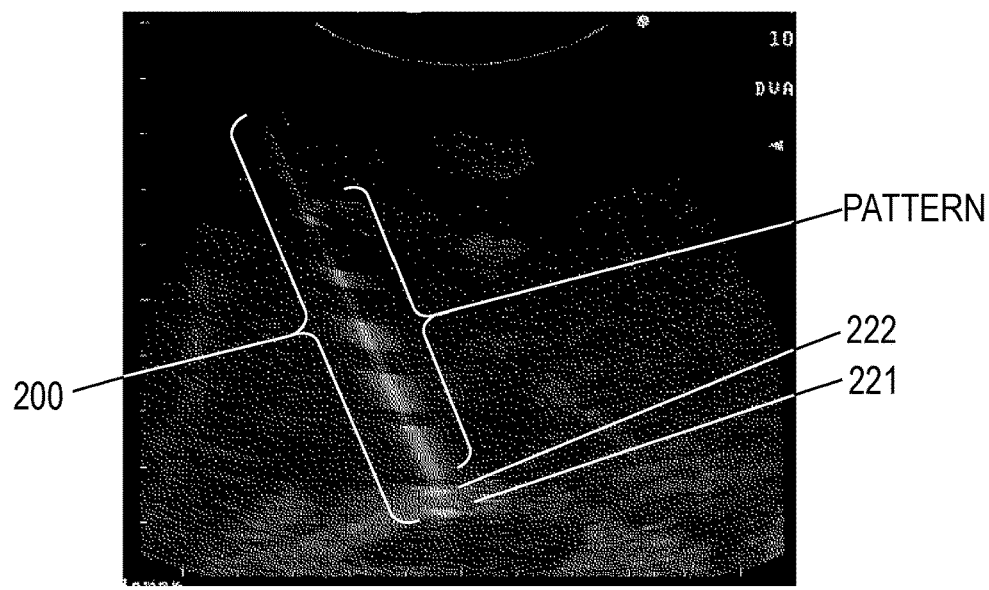
FIG. 24 shows how a needle provided with a pattern that causes reflection characteristics of ultrasound to change is inserted into a target object and detected by ultrasound.

The surface of the needle 200 may be subjected to treatment that causes reflection characteristics of ultrasound to change in a predefined pattern. FIG. 24 shows how a needle provided with a pattern that causes reflection characteristics of ultrasound to change is inserted into a target object and detected by ultrasound. It can be seen that tips 221 and 222 of the needle 200 and the pattern have been detected. By thus applying a pattern that causes the reflection characteristics of ultrasound to change to the needle, it is easy to recognize the position at which the magnetic marker 100 is arranged. Similarly, the magnetic marker 100 may be subjected to treatment that causes the reflection characteristics of ultrasound to change in a predefined pattern. If different patterns are applied to the first rod 110, the second rod 120, and the third rod 130, the state of arrangement of the magnetic marker 100 can be recognized upon arrangement of the magnetic marker 100. Both the needle 200 and the magnetic marker 100 may be subjected to treatment that causes the reflection characteristics of ultrasound to change in a predefined pattern or only one of them may be subjected to such a treatment.

<Method of Arranging Magnetic Marker>

Figure 25:
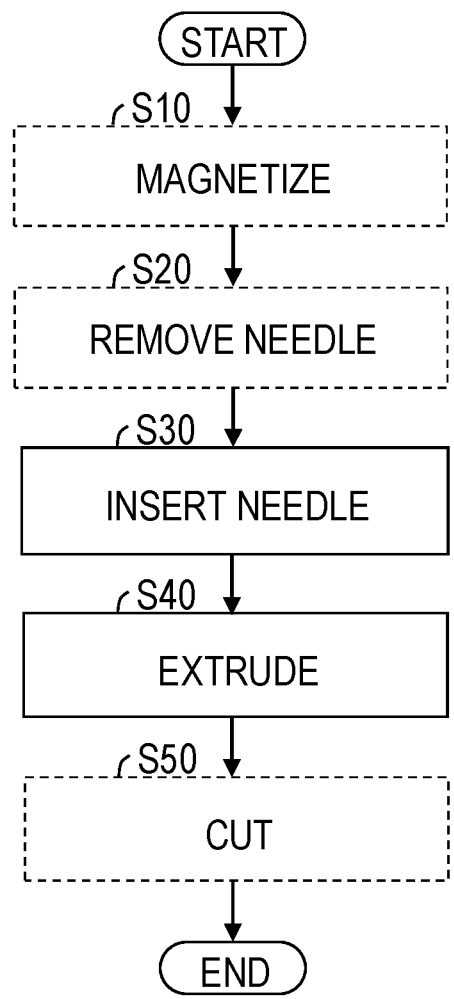
FIG. 25 shows a process flow of a method of arranging magnetic marker.

FIG. 25 shows a process flow of a method of arranging magnetic marker. The steps shown with dotted lines are steps that are unnecessary in some cases. The magnetic marker 100 may be magnetized in advance or may be used after it is magnetized by the user himself. If an unmagnetized magnetic marker 100 has been inserted into the needle 200, the user places the permanent magnet 300 as in FIG. 17 or FIG. 20 to magnetize the magnetic marker 100 (S10: magnetization step). The magnetic marker set 10 that also contains the permanent magnet 300 as shown in FIG. 17 may be distributed. In that case, the user would remove the needle 200 from the permanent magnet 300 (S20: needle removing step). A previously magnetized magnetic marker set 10 without the permanent magnet 300 may also be distributed. The user inserts the needle 200 with the magnetic marker 100 inserted in the hole 210 into a target object such that the tip 221 of the needle 200 lies at a position where the magnetic marker 100 is to be arranged (S30: needle insertion step). For example, the user inserts the needle 200 into a breast so that the tip 221 is at the location of a breast cancer. Then, the user extrudes the magnetic marker 100 from the hole 210 such that the first connecting portion 115 points toward a device that detects the magnetic marker 100 (S40: extrusion step). For example, if the magnetic marker 100 is arranged within a breast, the magnetic marker 100 may be extruded so that the first connecting portion 115 points to the outside of the breast. The user may also create a state that does not require the user to consider the orientation of the first connecting portion 115 in the extrusion step (S40) by inserting the needle such that the extruded first connecting portion 115 points to the outside of the breast in the needle insertion step (S30). Then, if the thread 143 is used as the draw-in mechanism 140, the thread 143 is cut (S50: cutting step).

DESCRIPTION OF REFERENCE NUMERALS 10 magnetic marker set
100 magnetic marker
110 first rod
115 first connecting portion
120 second rod
125 second connecting portion
130 third rod
135 elastic body
140 draw-in mechanism
141 fixing portion
142 holding portion
143 thread
200 needle
210 hole
221, 222 tip
300 permanent magnet
310 slit
400 accommodation means
500 operational portion
510 extrusion means
520 inner tube
521 inner tube side hole
530 inner-inner tube
531 inner-inner tube side hole
550 cutting means
560 slit
570 knob
580 end portion

What is claimed is:

1. A magnetic marker set comprising:
a magnetic marker including a first rod and a second rod each formed of a stick-shaped magnetic substance with residual magnetization characteristics, and a stick-shaped third rod; and
a needle with a hole in a longitudinal direction thereof, wherein
the magnetic marker further includes
a first connecting portion at which one longitudinal end of the first rod and one longitudinal end of the second rod are rotatably connected, and
a second connecting portion at which an other longitudinal end of the second rod and one longitudinal end of the third rod are rotatably connected,
the magnetic marker is inserted into the hole and has been magnetized such that an orientation of a magnetic field reverses at the first connecting portion, and
the magnetic marker set further includes
a draw-in mechanism that has a thread arranged in the hole and brings an other longitudinal end of the first rod and an other longitudinal end of the third rod close to each other when the magnetic marker is extruded from the hole,
a cutting portion, including at least an edge configured to cut the thread, and
an inner tube arranged in the hole and an inner-inner tube arranged in the inner tube,
the magnetic marker is positioned so as to be extruded from the hole in the order of the first rod, the second rod, and the third rod, with one end of the thread being fixed to the other longitudinal end of the first rod, and the thread being movably held at the other longitudinal end of the third rod,
the cutting portion is constituted by an inner tube side hole formed in a side of the inner tube and an inner-inner tube side hole formed in a side of the inner-inner tube,
when the inner tube side hole and the inner-inner tube side hole are placed at a position in which the inner tube side hole and the inner-inner tube side hole face each other, the thread passes through the inner tube side hole and the inner-inner tube side hole, and
the thread is cut by placing the inner tube side hole and the inner-inner tube side hole at a position in which the inner tube side hole and the inner-inner tube side hole do not face each other.

2. The magnetic marker set according to claim 1, wherein each of the first connecting portion and the second connecting portion is formed of a coil-shaped elastic body.

3. The magnetic marker set according to claim 1, wherein the needle and the magnetic marker or one of the needle and the magnetic marker have/has been treated such that reflection characteristics of ultrasound change in a predefined pattern.

4. The magnetic marker set according to claim 1, further comprising:
an extruder, configured to extrude the magnetic marker from the needle.

5. A method of arranging magnetic marker using the magnetic marker set according to claim 1, the method executing:
needle insertion for inserting the needle with the magnetic marker inserted in the hole such that a tip of the needle lies at a position where the magnetic marker is to be arranged; and
extrusion for extruding the magnetic marker from the hole such that the first connecting portion points toward a device that detects the magnetic marker.

6. The magnetic marker set according to Claim 1, further comprising:
a permanent magnet, which is a plate with one face being an N pole and another face being an S pole and has a slit penetrating from the one face to the other face; and
a housing configured to accommodate the needle having the magnetic marker inserted therein, with the needle inserted in the slit such that either face of the permanent magnet aligns with a position of the first connecting portion.

7. The magnetic marker set according to Claim 1, further comprising:
a permanent magnet, which is in a shape of a plate with one face being an N pole and another face being an S pole; and
a housing configured to accommodate the needle having the magnetic marker inserted therein, with the needle positioned such that a position of the first connecting portion is on a same plane as either face of the permanent magnet and that a normal direction of the plane coincides with a longitudinal direction of the second rod.

8. A magnetic marker set comprising:
a magnetic marker including a first rod and a second rod each formed of a stick-shaped magnetic substance with residual magnetization characteristics, and a stick-shaped third rod; and
a needle with a hole in a longitudinal direction thereof, wherein
the magnetic marker further includes
a first connecting portion at which one longitudinal end of the first rod and one longitudinal end of the second rod are rotatably connected, and
a second connecting portion at which an other longitudinal end of the second rod and one longitudinal end of the third rod are rotatably connected,
the magnetic marker is inserted into the hole and has been magnetized such that an orientation of a magnetic field reverses at the first connecting portion, and
the magnetic marker set further includes
a draw-in mechanism that brings an other longitudinal end of the first rod and an other longitudinal end of the third rod close to each other when the magnetic marker is extruded from the hole,
a permanent magnet, which is a plate with one face being an N pole and another face being an S pole and has a slit penetrating from the one face to the other face; and
a housing configured to accommodate the needle having the magnetic marker inserted therein, with the needle inserted in the slit such that either face of the permanent magnet aligns with a position of the first connecting portion.

9. The magnetic marker set according to claim 8, wherein
a thickness of the permanent magnet is half a length of the second rod or more, and
the needle is held such that the second rod is at a position of the permanent magnet.

10. The magnetic marker set according to Claim 8, wherein
the draw-in mechanism has a thread arranged in the hole, and
the magnetic marker is positioned so as to be extruded from the hole in the order of the first rod, the second rod, and the third rod, with one end of the thread being fixed to the other longitudinal end of the first rod, and the thread being movably held at the other longitudinal end of the third rod.

11. The magnetic marker set according to claim 10, further comprising:
a cutting portion, including at least an edge configured to cut the thread.

12. The magnetic marker set according to claim 11, further comprising:
an inner tube arranged in the hole and an inner-inner tube arranged in the inner tube, wherein
the cutting portion is constituted by an inner tube side hole formed in a side of the inner tube and an inner-inner tube side hole formed in a side of the inner-inner tube,
when the inner tube side hole and the inner-inner tube side hole are placed at a position in which the inner tube side hole and the inner-inner tube side hole face each other, the thread passes through the inner tube side hole and the inner-inner tube side hole, and
the thread is cut by placing the inner tube side hole and the inner-inner tube side hole at a position in which the inner tube side hole and the inner-inner tube side hole do not face each other.

13. A method of arranging magnetic marker using the magnetic marker set according to claim 8, the method executing:
needle insertion for inserting the needle with the magnetic marker inserted in the hole such that a tip of the needle lies at a position where the magnetic marker is to be arranged; and
extrusion for extruding the magnetic marker from the hole such that the first connecting portion points toward a device that detects the magnetic marker.

14. A magnetic marker set comprising:
a magnetic marker including a first rod and a second rod each formed of a stick-shaped magnetic substance with residual magnetization characteristics, and a stick-shaped third rod; and
a needle with a hole in a longitudinal direction thereof, wherein
the magnetic marker further includes
a first connecting portion at which one longitudinal end of the first rod and one longitudinal end of the second rod are rotatably connected, and
a second connecting portion at which an other longitudinal end of the second rod and one longitudinal end of the third rod are rotatably connected,
the magnetic marker is inserted into the hole and has been magnetized such that an orientation of a magnetic field reverses at the first connecting portion, and
the magnetic marker set further includes
a draw-in mechanism that brings an other longitudinal end of the first rod and an other longitudinal end of the third rod close to each other when the magnetic marker is extruded from the hole,
a permanent magnet, which is in a shape of a plate with one face being an N pole and another face being an S pole, and
a housing configured to accommodate the needle having the magnetic marker inserted therein, with the needle positioned such that a position of the first connecting portion is on a same plane as either face of the permanent magnet and that a normal direction of the plane coincides with a longitudinal direction of the second rod.

15. The magnetic marker set according to claim 14, wherein
a thickness of the permanent magnet is half a length of the second rod or more, and
the needle is held such that the second rod is at a position of the permanent magnet.

16. The magnetic marker set according to claim 14, wherein
the draw-in mechanism has a thread arranged in the hole, and
the magnetic marker is positioned so as to be extruded from the hole in the order of the first rod, the second rod, and the third rod, with one end of the thread being fixed to the other longitudinal end of the first rod, and the thread being movably held at the other longitudinal end of the third rod.

17. The magnetic marker set according to claim 16, further comprising:
a cutting portion, including at least an edge configured to cut the thread.

18. The magnetic marker set according to claim 17, further comprising:
an inner tube arranged in the hole and an inner-inner tube arranged in the inner tube, wherein
the cutting portion is constituted by an inner tube side hole formed in a side of the inner tube and an inner-inner tube side hole formed in a side of the inner-inner tube,
when the inner tube side hole and the inner-inner tube side hole are placed at a position in which the inner tube side hole and the inner-inner tube side hole face each other, the thread passes through the inner tube side hole and the inner-inner tube side hole, and
the thread is cut by placing the inner tube side hole and the inner-inner tube side hole at a position in which the inner tube side hole and the inner-inner tube side hole do not face each other.

19. A method of arranging magnetic marker using the magnetic marker set according to claim 14, the method executing:
needle insertion for inserting the needle with the magnetic marker inserted in the hole such that a tip of the needle lies at a position where the magnetic marker is to be arranged; and
extrusion for extruding the magnetic marker from the hole such that the first connecting portion points toward a device that detects the magnetic marker.

* * * * *